ABSTRACT

United States Patent [19]
Wilkes

[11] 4,016,185
[45] Apr. 5, 1977

[54] PRODUCTION OF CARBOXYLIC ACIDS FROM PARAFFINS AND CARBON DIOXIDE

[75] Inventor: John B. Wilkes, Richmond, Calif.

[73] Assignee: Chevron Research Company, San Francisco, Calif.

[22] Filed: Dec. 11, 1975

[21] Appl. No.: 639,864

[52] U.S. Cl. .............................. 260/413; 260/533 R
[51] Int. Cl.² .................. C07C 51/00; C07C 51/15
[58] Field of Search ............... 260/413, 533 R, 451, 260/604 R, 682

[56] References Cited
UNITED STATES PATENTS 1,697,265  1/1929  Ellis .................................. 260/451

*Primary Examiner*—Winston A. Douglas
*Assistant Examiner*—P. E. Konopka
*Attorney, Agent, or Firm*—J. A. Buchanan, Jr.; John Stoner, Jr.; W. Keith Turner

[57] ABSTRACT

Carboxylic acids are prepared from high-molecular-weight paraffins by vapor phase cracking at a temperature of at least about 500°C and a residence time of from about 0.1 seconds to about 10 seconds in the presence of carbon dioxide.

5 Claims, No Drawings

PRODUCTION OF CARBOXYLIC ACIDS FROM PARAFFINS AND CARBON DIOXIDE

BACKGROUND OF THE INVENTION

Thermal or vapor phase cracking of saturated hydrocarbons to prepare unsaturated hydrocarbons has been known since the latter part of this century. Many important features, such as the production of olefin and aromatic hydrocarbons and the use of steam to prevent carbon formation, have been reported.

It has now been discovered that recoverable yields of carboxylic acids are prepared by vapor-phase cracking of high-molecular-weight paraffins under select conditions in the presence of carbon dioxide. In particular, it has been found that paraffins containing at least 12 carbon atoms when cracked at a temperature of at least 500° C and a residence time of from about 0.1 seconds to about 10 seconds in the presence of from about 0.5 to about 5 mols of carbon dioxide per mol of hydrocarbon are converted at recoverable yields to carboxylic acids.

Carbon dioxide has been employed in vapor phase dehydrogenation of saturated and unsaturated hydrocarbons under conditions which promote the dehydrogenation reaction; but has not been employed to produce carboxylic acids. For example, U.S. Pat. No. 2,775,631 granted Dec. 25, 1956 describes vapor phase dehydrogenation of $C_5$ to $C_8$ olefins to prepare aromatics in the presence of carbon dioxide and a molybdenum oxide catalyst; U.S. Pat. No. 3,406,219 granted Oct. 15, 1968 describes the dehydrogenation of ethylbenzene with at least 3 mols of carbon dioxide in the presence of a Fischer-Tropsch catalyst to prepare styrene; and U.S. Pat. No. 3,505,422 granted Apr. 7, 1970 describes the dehydrogenation of hydrocarbons by a catalytic process in which minor amounts of carbon dioxide are added to steam to increase the consumption of hydrogen produced.

Carbon dioxide has been employed in the vapor phase conversion of para-xylene to prepare terephthalic acid. For example, Higuchi et al, Kogyo Kagaku Zasshi, 1968, 71(10), 1663-6 describes the thermal decomposition of p-xylene diluted in carbon dioxide at a temperature of 860° C to 1050° C to prepare the aromatic acid.

Carbon dioxide has also been employed in carboxylations effected by ionizing radiation. For example, McKusick et al, Journal of the American Chemical Society, 1960, 82, 723 describe irradiation of a mixture of hydrocarbon and carbon dioxide with high energy electrons to give carboxylic acids.

While carbon dioxide has been employed to promote dehydrogenation by reacting with hydrogen to form water and carbon monoxide, the process of the present invention employs relatively mild vapor phase cracking conditions and a high molecular weight paraffin which are suitable to effect reaction between the paraffin and carbon dioxide to form carboxylic acids. This should not be confused with the formation of aromatic carboxylic acids under extreme conditions of high temperature. At high temperatures, above about 1000° C, carbon dioxide can oxidize the aromatic to its corresponding acid, while being reduced to carbon monoxide. Under conditions of this invention carbon dioxide is not an oxidizing agent.

SUMMARY OF THE INVENTION

In accordance with the process of this invention carboxylic acids are prepared by vapor phase cracking of high-molecular-weight paraffins at a temperature of at least 500° C and a residence time of from about 0.1 seconds to about 10 seconds in the presence of from about 0.5 to about 5 mols of carbon dioxide per mol of paraffin.

DETAILED DESCRIPTION OF THE INVENTION

As used herein the term "high-molecular-weight" paraffin encompasses paraffins having a molecular weight of at least 168 and containing at least 12 carbon atoms, preferably from about 12 to about 40 carbon atoms. High-molecular-weight paraffins are generally obtained from commercial petroleum based processes. Suitable commercial processes for producing high-molecular-weight paraffins include, for example, molecular sieve adsorption from kerosene, urea dewaxing of gas oil and vacuum distillates, and waxes by chilling and recrystallization. Suitable paraffins are also available from the Fischer-Tropsch reaction of hydrogen and carbon monoxide and from distillation of wood, peat and lignite.

Accordingly, the process of this invention is satisfactory for converting individual paraffins, for example, heptadecane; or mixtures of paraffins, for example petroleum wax, to carboxylic acids. The conversion of paraffins to carboxylic acids is carried out in the vapor phase at relatively low cracking temperatures. In general a temperature of about 500° C to about 700° C is satisfactory, while temperatures of from about 550° C to about 650° C are preferred. Atmospheric and super-atmospheric pressures are suitable. Under these conditions it has been found that a residence time of from about 0.1 seconds to about 10 seconds is required. The shorter residence times should be used at the higher temperatures, and the longer residence times at the lower temperatures. If the residence time is excessive, the acids which are initially formed will be decarboxylated. As those skilled in the art can appreciate, residence time and the physical dimensions of the cracker determine volumetric flow rates for the paraffin feed and the carbon dioxide feed.

The essence of the process of this invention resides in the combined presence of paraffin and carbon dioxide. It has been found that by cracking the paraffin in a carbon dioxide atmosphere that carboxylic acids are formed. For satisfactory conversion from about 0.5 to 5 mols of carbon dioxide per mol of hydrocarbon is desirable; from about 1 to about 3 mols is preferable.

It is believed that under the cracking conditions of the process of this invention a free radical reaction takes place during which carbon dioxide combines with a paraffin radical to form an acid. A variety of free radical schemes can be proposed. For example,

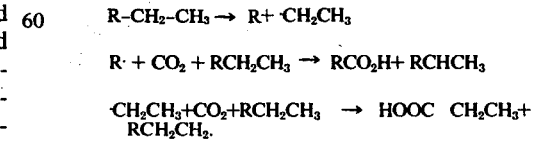

etc.

Accordingly, although high-molecular-weight paraffins are employed as starting materials, the process of this invention can be employed to prepare a wide variety of carboxylic acids ranging from formic acid to the high-molecular-weight acids.

The following examples further illustrate the practice of this invention.

EXAMPLES

In the examples, a hydrocarbon feed was contained in a steam-jacketed buret, and was pumped into the reactor by a heated diaphragm pump. Water or a gaseous diluent can be mixed with the hydrocarbon feed after it leaves the pump and before it enters the reactor. The reactor consisted of a series of three coils of stainless steel tubing in three individually heated baths of molten lead. The first coil of 20 feet of 0.18 inch (inside diameter) tubing served as a preheater and vaporizer. The two subsequent coils of 0.18 inch tubing, 10 feet and 20 feet long, served as the reactor. The products from the reactor were first passed through a heat exchanger with hot water in the jacket. The high-boiling components were largely condensed, and were removed through a separator heated with hot water. The uncondensed products were then passed through a condenser cooled with circulating ice water, a condenser cooled with dry ice and a trap immersed in dry ice. The gaseous products which remained were passed through a wet test meter to measure their volume and were then vented.

EXAMPLE 1 — CRACKING $C_{17}$-$C_{19}$ PARAFFINS WITH $CO_2$

The feed was obtained by careful fractionation of a mixture of n-paraffins. Analysis by gas chromatography showed that it contained 9.5 weight percent linear $C_{17}$ paraffin, 79.1% linear $C_{18}$ paraffin, 10.3% linear $C_{19}$ paraffin and 1.1% branched $C_{18}$-$C_{20}$ paraffin. This paraffin was fed to the reactor for a period of 2 hours at the rate of 18–20 cc/min., along with 2 liters/min., measured at room temperature and pressure, of $CO_2$. The vaporizer was maintained at 723° F to 838° F, and the two baths containing the reactors were maintained at 1090° F–1105° F during the reaction. About 1780 g of paraffin were fed. About 1290 g of material containing feed and $C_6$-$C_{16}$ olefins was obtained from the first separator, and 172 g of $C_4$-$C_9$ olefins were obtained from the other separators and cold traps, after the olefins which were gaseous at room temperature were allowed to evaporate.

Gas chromatographic analysis of the larger fraction showed that it contained 365 g of olefins. A 100-g portion of this material was extracted with approximately 0.5 N methanolic sodium hydroxide solution, and the extract was filtered. Acids in the filtrate were then esterified by refluxing with methanol and sulfuric acid. The cooled product was diluted with water and extracted with $CS_2$ to extract esters. An infrared spectrum of the $CS_2$ extract showed strong bands at 1740 and 1160 cm-116 $^1$, corresponding to ester C=O and C-OR vibrations. Gas-liquid chromatography of the $CS_2$ extract on a poly(diethyleneglycol succinate) column gave several peaks. Comparison of retention times to those of authentic methyl esters of fatty acids showed the products to be as follows:

TABLE 1

| Peak Retention Time, Minutes | Area % | Identification by Retention Time |
|---|---|---|
| 14.0 | 11.0 | $C_9$ ester |
| 20.8 | 5.1 | Paraffin or $C_{12}$ ester |

TABLE 1-continued

| Peak Retention Time, Minutes | Area % | Identification by Retention Time |
|---|---|---|
| 24.5 | 11.8 | $C_{13}$ ester |
| 29.6 | 32.0 | Probable $C_{15}$ ester |
| 32.7 | 1.8 | $C_{16}$ ester |
| 36.7 | 6.3 | Probable $C_{17}$ ester |

The products with retention times of 24.5, 29.6 and 36.7 minutes were separately trapped from the gas chromatograph effluent, and examined by infrared spectroscopy. All displayed strong absorbence bands at 1740, 1160, and 1030 cm$^{-1}$, typical of esters. All also had an absorbence bond at 1780 cm$^{-1}$, indicating a possible lactone fraction or a double bond conjugated with the carbonyl group.

EXAMPLE 2 — CARBOXYLIC ACIDS BY CRACKING WAX IN THE PRESENCE OF $CO_2$ 36 cc/min. of a $C_{20}$-$C_{40}$ paraffin wax with a high content of linear paraffins, and 2000 cc/min, measured at room temperature and pressure, of $CO_2$ were fed to the reactor for a period of about 2.5 hours. The vaporizer was maintained at 665° F–820° F, and the reactor baths at 1040° F–1125° F. 1786 g of product were collected from the first separator and 177 g of product from the other separators and traps. The latter products contained principally $C_4$-$C_9$ olefins, and were investigated for acid content.

Titration of a sample of the hydrocarbon layer gave an acid number of 11.8. A sample of this material was extracted with 0.5N sodium hydroxide solution. The extract was added to a mixture of sulfuric acid and methanol, and refluxed 2 hours to convert the extracted acids to methyl ester. The mixture was cooled, diluted with water, and extracted with $CS_2$. Infrared analysis showed that the extracted product consisted mainly of esters. The esters were analyzed by gas chromatography on a poly(diethylene glycol succinate) column, and by comparison of retention times to those of known samples of methyl esters. As the lower esters (formic, acetic esters) would not be extracted by $CS_2$, another sample of product was extracted with aqueous sodium hydroxide solution, the extract was acidified to pH 3 with phosphoric acid, and the lower acids were identified by gas chromatography on a Poropak column. The combined results of these analyses gave the following distribution of acids:

TABLE II

| Acid | % of Acid | Branched, % |
|---|---|---|
| Formic | 6 | — |
| Acetic | 17 | — |
| Propionic | 17 | — |
| Butyric | 12 | 13 |
| Valeric | 21 | 1 |
| Hexanoic | 12 | 20 |
| Heptanoic | 8 | 26 |
| Octanoic | 5 | — |
| Nonanoic | 1.5 | — |
| Decanoic | 0.5 | — |

Higher acids were not present in this fraction, as they would be condensed in the first product separator.

A run was made as above; however, instead of $CO_2$, liquid water was fed at 4–6 ml/min. The trap contents had an acid number of 0.9, showing the absence of significant amounts of acid.

What is claimed is:

1. A process for preparing saturated carboxylic acids by vapor-phase cracking of high-molecular-weight paraffins, having a molecular weight of at least 168 and containing from about 12 to about 40 carbon atoms, in the presence of from about 0.5 to about 5.0 mols of carbon dioxide per mol of paraffin; wherein said cracking is carried out under conditions such that carbon dioxide is not an oxidizing agent; said conditions including a temperature of from about 500° C to about 700° C and a residence time of from about 0.1 seconds to about 10 seconds.

2. A process according to claim 1 wherein said paraffins are linear $C_{17}$–$C_{19}$ paraffins.

3. A process according to claim 1 wherein said paraffins are $C_{20}$-$C_{40}$ paraffins.

4. A process according to claim 1 wherein said temperature is from about 550° C to about 650° C.

5. A process according to claim 1 wherein cracking is carried out in the presence of from about 1 to about 3 mols of carbon dioxide per mol of paraffin.

* * * * *